United States Patent [19]

Van den Berg et al.

[11] Plant 4,733

[45] Jun. 2, 1981

[54] IMPATIENS PLANT

[75] Inventors: Cornelis P. Van den Berg; James C. Mikkelsen, both of Ashtabula, Ohio

[73] Assignee: Mikkelsens, Inc., Ashtabula, Ohio

[21] Appl. No.: 103,087

[22] Filed: Dec. 12, 1979

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Telstar, and particularly characterized by the combined characteristics of excellent self-branching; spreading habit; highly variegated foliage; orchid/violet flowers; suitability for growing both outside in full sunlight and in hanging baskets; and by its good keeping quality both outside in full sunlight and in hanging baskets.

1 Drawing Figure

1

The present invention relates to a new and distinct cultivar of impatiens plant, hereinafter referred to by the cultivar name Telstar.

Telstar is the product of a planned breeding program and was originated from a cross made by us in Ashtabula, Ohio. The seed parent was an unnamed cultivar identified by seedling number 77-499-1, and the pollen parent was Constellation, a commercial but unpatented cultivar. Asexual reproduction by terminal or stem cuttings taken by us in Ashtabula, Ohio has shown that the combination of unique characteristics as herein disclosed for Telstar are stable and retained through successive generations of asexual reproduction.

The following characteristics distinguish Telstar from both its parent varieties and other cultivated impatiens of this type known and used in the floriculture industry:

1. Telstar was selected especially for its superior self-branching and spreading habits, which makes the cultivar highly suitable for growing in a hanging basket.
2. Flowers are orchid/violet, darker than those of Constellation, and have a tendency to be slightly cupped.
3. Flowers appear in an early stage of plant development, and plant continues to flower throughout the growing season.
4. Flowers are 50 mm. in diameter, comparable to those of Sunfire, disclosed in application Serial Number 103,090 filed Dec. 12, 1979.
5. Foliage is highly variegated, having a dark green edge with a cream midvein area, split by the red midvein.
6. Telstar is highly productive as a cutting producer due to its extraordinary self-branching habit.
7. Spreading habit and self-branching make plant highly suitable for growing in hanging basket.
8. Telstar exhibits good keeping qualities both in hanging baskets and if grown outside in full sunlight in Ashtabula, Ohio where it will flower from planting date in early June until frost kills the plant.
9. Growth rate is comparable to that of Sunfire, producing a dome-shaped plant of 30 cm. high and 60 cm. in diameter in 60 days after planting outside, starting from a plant in a 10 cm. pot, or a saleable 8" to 10" hanging basket, starting from 3 rooted cuttings per basket, in approximately 90 days, both as tested in Ashtabula, Ohio.

2

The accompanying colored photograph, taken in June, 1979, illustrates the flowers and foliage colors of Telstar, with the colors as true as it is reasonably possible to obtain in a colored reproduction of this type.

The following is a detailed description of the new impatiens cultivar based on plants produced under commercial practices in Ashtabula, Ohio both in the greenhouses of Mikkelsens Inc., and outdoors in full sunlight. Color references are made to the Royal Horticultural Society Colour Chart except where general terms of ordinary dictionary significance are used.

Parentage:

A controlled cross of Mikkelsen seedling number 77-499-1 as the seed parent and cultivar Constellation as the pollen parent.

Propagation:

(A) *Type cutting.*—Short tip cutting with stems up to 2 cm. long.

(B) *Time to root.*—10–12 days at 20° C. summer. 14–16 days at 20° C. winter.

(C) *Rooting habit.*—Abundant, fibrous.

Plant description:

(A) *Form.*—Spreading, close internoded, extremely self-branching herb, which produces in approximately 60 days a dome-shaped plant approximately 30 cm. high and 60 cm. in diameter when grown outside, starting from a plant in a 10 cm. pot.

(B) *Habit of growth.*—Rate of growth moderate for this type of plant. Vegetative shoots are formed at the lower nodes and flowers at the higher nodes.

(C) *Foliage description.*—Leaves simple, lower leaves in whorls of 3, upper leaves in whorls of 6, sometimes more. (1) Size: Average full grown leaf 120 mm. long × 40 mm. wide. Full grown leaves have petioles up to 40 mm. long, young leaves very short to no petioles. (2) Shape: Ovate-oblong, apex acuminate, base attenuate. (3) Texture: Leathery, glabrous. (4) Margin: Serrulate. (5) Color: Young foliage: top side outer area yellow-green 147A, inner area yellow-orange 16B, infused with red; under side outer area yellow-green 147A, inner area greyed-red 180B-C. Mature foliage: top side outer area yellow-green 147A, inner area yellow 11B-C, very slightly infused with red; under side outer area greyed-red 182-A, inner area greyed-red 180B-C. (6) Veination: Pinnate; main vein young foliage red 47A; main vein mature foliage red 47B-C.

Flowering description:

(A) *Flowering habits.*—Relatively floriferous, with single flowers occurring progressively around the whorl of leaves; flower form is slightly cupped.

(B) *Natural flowering season.*—Flowering is indeterminate and occurs throughout the year.

(C) *Flower buds.*—Conical, covered with 3 sepals; upper 2 sepals 12 mm. long × 6 mm. wide, acuminate; lower sepal 12 mm. long × 10 mm. wide, petaloid, asymmetrically funnel form, cuspidate, with a hollow, nearly colorless spur, 45 mm. long if full grown.

(D) *Flowers borne.*—On pedicels, color red 49B-C, 40–50 mm. long.

(E) *Quantity of flowers.*—One flower per leaf, occurring progressively around the whorl of leaves.

(F) *Petals.*—(1) Shape: All heart-shaped. (2) Color: Under periods of high light, the top side when opening is near 77C, with a light eye and a small red blotch 54B at the base of each of the two lower petals. In high light conditions, the petals fade to 77D or 75B. Under low light and low temperature conditions, the color intensity increases to 77B on opening, and fades at maturity to 77C-D; under side purple 77D. (3) Number of petals: Five, the 4 lower petals being united in lateral pairs. (4) Size of petals: 25 mm. long × 20 mm. wide, flowers 50 mm. in total diameter.

(G) *Reproductive organs.*—(1) Stamens: Five in number, lower stamen shorter than the others. (a) Anthers: Hooded shape, white to cream white in color. (b) Pollen color: White to cream white. (c) Stamens united in an asymmetrical tube, covering the ovary. (2) Pistels: (a) Stigma shape: Five pointed star, colorless, infused with red. (b) Style shape: Very short, dome-shaped. (c) Style Color: colorless, infused with red. (d) Ovary: 5 celled, 5 mm. long, color green, apex red striped; explosively dehiscent.

Disease resistance:

No General plant diseases observed to date. However, two dotted spider mite can cause plant injury, and thrips can cause injury and stunting of the growing tip.

We claim:

1. A new and distinct cultivar of Impatiens known by the cultivar name Telstar, as described and illustrated, and particularly characterized as to novelty by the combined characteristics of excellent self-branching; spreading habit; highly variegated foliage; orchid/violet flowers; suitability for growing both outside in full sunlight and in hanging baskets; and by its good keeping quality both outside in full sunlight and in hanging baskets.

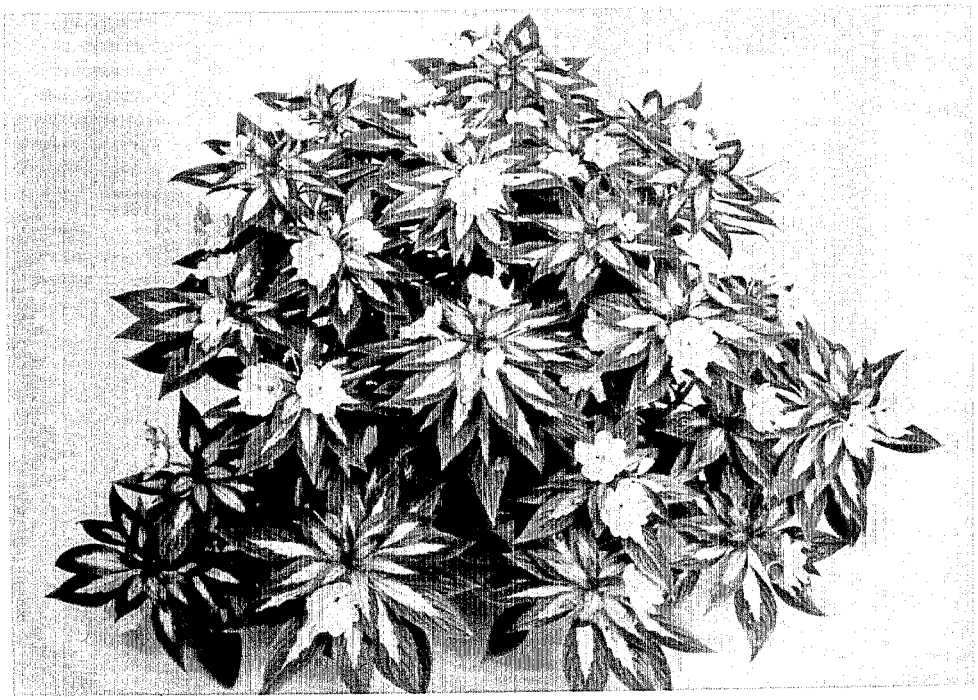

* * * * *